US008038646B2

(12) United States Patent  
Kawano

(10) Patent No.: US 8,038,646 B2  
(45) Date of Patent: Oct. 18, 2011

(54) BODY-INSERTABLE APPARATUS AND MANUFACTURING METHOD THEREOF

(75) Inventor: Hironao Kawano, Nagano (JP)

(73) Assignee: Olympus Corporation, Tokyo (JP)

( * ) Notice: Subject to any disclaimer, the term of this patent is extended or adjusted under 35 U.S.C. 154(b) by 895 days.

(21) Appl. No.: 11/658,285

(22) PCT Filed: Oct. 14, 2005

(86) PCT No.: PCT/JP2005/019356
§ 371 (c)(1),
(2), (4) Date: Jan. 23, 2007

(87) PCT Pub. No.: WO2006/041222
PCT Pub. Date: Apr. 20, 2006

(65) Prior Publication Data
US 2008/0294101 A1 Nov. 27, 2008

(30) Foreign Application Priority Data

Oct. 15, 2004 (JP) ................................. 2004-302149

(51) Int. Cl.
*A61M 31/00* (2006.01)
(52) U.S. Cl. .......... 604/67; 604/131; 604/132; 604/133; 604/891.1; 600/16
(58) Field of Classification Search ............... 604/67, 604/131–133, 891.1; 600/16
See application file for complete search history.

(56) References Cited

U.S. PATENT DOCUMENTS 3,485,235 A 12/1969 Felson
3,506,005 A * 4/1970 Maccarone et al. .......... 604/132
3,840,009 A * 10/1974 Michaels et al. ........... 604/892.1
3,955,901 A * 5/1976 Hamilton ...................... 417/395

(Continued)

FOREIGN PATENT DOCUMENTS

CN 1519040 A 8/2004

(Continued)

OTHER PUBLICATIONS

Japanese Official Action dated Jul. 6, 2010 together with an English language translation.

(Continued)

*Primary Examiner* — Nicholas D Lucchesi
*Assistant Examiner* — Scott Medway
(74) *Attorney, Agent, or Firm* — Scully, Scott, Murphy & Presser, P.C.

(57) ABSTRACT

A body-insertable apparatus which can make the volume smaller by simplifying a mechanism taking in or throwing out predetermined fluid is realized. The body-insertable apparatus has a configuration having, in a housing, a balloon member, a communication adjusting mechanism, a control circuit, and a power source part and forms a storage chamber by the balloon member and an outer circumferential member (sheet holding substrate and part of the housing) covering the outer surface of the balloon member. In the body-insertable apparatus, a first communication pipe communicated with the inner space of the balloon member and a second communication pipe communicated with the outer space are formed. The communication adjusting mechanism communicates the first communication pipe with the second communication pipe based on an electric current output from the control circuit. The inner space of the balloon member is communicated with the outside of the body-insertable apparatus. The outside fluid is flowed into the storage chamber via an inlet with the contracting operation of the balloon member.

7 Claims, 10 Drawing Sheets

U.S. PATENT DOCUMENTS

| | | | |
|---|---|---|---|
| 4,033,479 A * | 7/1977 | Fletcher et al. | 222/61 |
| 4,041,944 A * | 8/1977 | Rhodes | 604/6.1 |
| 4,203,441 A * | 5/1980 | Theeuwes | 604/892.1 |
| 4,335,835 A * | 6/1982 | Beigler et al. | 222/95 |
| 4,439,197 A | 3/1984 | Honda et al. | |
| 4,693,714 A * | 9/1987 | Lundback | 623/3.18 |
| 4,820,300 A * | 4/1989 | Pierce et al. | 623/3.23 |
| 5,150,820 A * | 9/1992 | McGill | 222/95 |
| 5,167,633 A * | 12/1992 | Mann et al. | 604/141 |
| 5,368,571 A * | 11/1994 | Horres, Jr. | 604/131 |
| 6,416,495 B1 * | 7/2002 | Kriesel et al. | 604/132 |
| 6,432,039 B1 * | 8/2002 | Wardle | 600/37 |
| 6,542,350 B1 * | 4/2003 | Rogers | 361/284 |
| 7,172,551 B2 * | 2/2007 | Leasure | 600/16 |
| 7,352,111 B2 * | 4/2008 | Bagwell | 310/328 |
| 7,367,968 B2 * | 5/2008 | Rosenberg et al. | 604/891.1 |
| 7,494,459 B2 * | 2/2009 | Anstadt et al. | 600/17 |
| 7,637,892 B2 * | 12/2009 | Steinbach et al. | 604/153 |
| 2004/0068224 A1 | 4/2004 | Couvillon, Jr. et al. | |
| 2004/0225188 A1 | 11/2004 | Kleen et al. | |

FOREIGN PATENT DOCUMENTS

| | | |
|---|---|---|
| JP | 38-16395 | 8/1963 |
| JP | 38-16396 | 8/1963 |
| JP | S57-163309 | 10/1982 |
| JP | S59-006033 | 1/1984 |
| JP | 62-240038 | 10/1987 |
| JP | 63-77450 | 4/1988 |
| JP | 02-019140 | 1/1990 |
| JP | 2-25210 | 2/1990 |
| JP | 02-036848 | 2/1990 |
| JP | 05-228128 | 9/1993 |
| JP | 2004-313784 | 11/2004 |
| WO | WO 99/37921 | 7/1999 |

OTHER PUBLICATIONS

Japanese Office Action dated Sep. 28, 2010 with English translation.

* cited by examiner

BODY-INSERTABLE APPARATUS AND MANUFACTURING METHOD THEREOF

TECHNICAL FIELD

The present invention relates to a body-insertable apparatus and performing at least one of taking in and discharging predetermined fluid in the body and a manufacturing method thereof.

This application is based upon and claims the benefit of priority from Japanese Patent Application No. 2004-302149, filed Oct. 15, 2004, the entire contents of which are incorporated herein by reference.

BACKGROUND ART

A body-insertable apparatus for taking in body fluid of a patient has been proposed. Specifically, the body-insertable apparatus has a configuration having a capsule-shaped sheathing case, a storage chamber arranged in the sheathing case and having the function of being communicated with the outside of the body-insertable apparatus and of storing body fluid, and a taking control mechanism controlling taking fluid in the storage chamber, wherein the taking control mechanism performs predetermined control upon reaching a predetermined position in a body such as a patient to take in body fluid so that the taken body fluid is stored in the storage chamber.

A conventional body-insertable apparatus has a configuration in which in order to generate a suction force for taking in body fluid, a negative pressure is generated by abruptly changing the volume of a storage chamber with the action of a spring member. Specifically, the conventional body-insertable apparatus incorporates a piston which functions as part of the outer wall portion (a member defining the outer circumference of a region holding a stored target) of the storage chamber, is supplied with a resilient force by a predetermined spring member in the direction in which the volume of the storage chamber is increased, and is supplied with a tension canceling the resilient force by a predetermined fixed string. In such configuration, the piston provided in the body-insertable apparatus is moved according to the resilient force supplied by the spring member when the fixed string is cut based on the function of the taking control mechanism. The volume of the storage chamber is increased with the movement of the spring member to generate a negative pressure in the storage chamber. A suction force is generated so that the body fluid or the like of a body is flowed into the storage chamber (for instance, see Japanese Patent Laid-Open Application No. H02-36848).

A body-insertable apparatus which directly supplies medication to an affected portion in a body by application of the above mechanism has been also proposed. Such body-insertable apparatus according to the above configuration employs a configuration in which medication is previously held in a storage chamber and a spring member supplies a resilient force in the direction in which the volume of the storage chamber is decreased. The resilient force of the spring member acts on a piston by cutting a fixed string. The medication held in the storage chamber is discharged with decrease in the volume of the storage chamber.

The conventional body-insertable apparatus must have the spring member for changing the volume of the storage chamber and has the problem of making the body-insertable apparatus larger. Such problem will be described below.

The body-insertable apparatus of the configuration having the spring member must secure a region housing the spring member therein. To minimize such region, a general body-insertable apparatus employs a configuration in which the spring member is held in the most compressed state before performing a body fluid taking or a medication discharging. The general spring member has the maximum compressibility of only about 70%. A region of at least about 30% of the entire length of the spring member must be secured for housing the spring member. The body-insertable apparatus having the spring member increases the volume by the region housing the spring member. The load of a body into which the apparatus is introduced becomes larger.

The present invention has been made in view of the above and an object of the present invention is to realize a body-insertable apparatus which can make the volume smaller by simplifying a mechanism taking in or discharging predetermined fluid.

DISCLOSURE OF INVENTION

A body-insertable apparatus according to one aspect of the present invention is introduced into a body, performs at least one of taking in and discharging predetermined fluid in the body, and includes a storage chamber storing the predetermined fluid; a flow generating unit that has an expansion and contraction film which expands and contracts with changes in the shape of the expansion and contraction film, and generates a flow state of the predetermined fluid between the storage chamber and the body based on the expanding and contracting of the expansion and contraction film; and a control unit that controls the expanding and contracting operations of the expansion and contraction film.

According to this body-insertable apparatus, since the flow generating unit that generates a flow state by changes in the shape of the expansion and contraction film is provided, the body-insertable apparatus can have a simple configuration without the conventional mechanism for generating a flow state, such as a spring member.

In the body-insertable apparatus, the flow generating unit may constitute at least part of an outer wall of the storage chamber.

In the body-insertable apparatus, the expansion and contraction film may be formed of elastic material.

In the body-insertable apparatus, the flow generating unit may include a balloon member that has a film-like member including in at least part thereof the expansion and contraction film, and that generates the flow state based on changes in an internal volume with the expanding and contracting.

In the body-insertable apparatus, the control unit may control the expanding and contracting of the expansion and contraction film by controlling a communication state between an inner space of the balloon member and an outer space of the body-insertable apparatus.

In the body-insertable apparatus, an opening communicating a space region covered by an outer surface of the balloon member and an inner surface of an outer circumferential member formed to cover an outer surface of the balloon member with a region other than the space region in the body-insertable apparatus may be provided in part of the outer circumferential member.

In the body-insertable apparatus, an opening communicating a space region covered by an outer surface of the balloon member and an inner surface of an outer circumferential member formed to cover an outer surface of the balloon member with an outer space of the body-insertable apparatus may be provided in part of the outer circumferential member.

In the body-insertable apparatus, the outer circumferential member may be provided with a plurality of the openings.

In the body-insertable apparatus, the control unit may control the expanding and contracting of the expansion and contraction film by controlling a communication state between a space region covered by an outer surface of the balloon member and an inner surface of an outer circumferential member formed to cover the outer surface and an outer space of the body-insertable apparatus.

In the body-insertable apparatus, the storage chamber may have an outer wall formed by the balloon member and an outer circumferential member formed to be spaced at a predetermined distance from an outer surface of the balloon member in an outside of the balloon member so as to store the predetermined fluid in a space region covered by the outer surface of the balloon member and an inner surface of the outer circumferential member.

In the body-insertable apparatus, an opening communicating the storage chamber with an outer space of the body-insertable apparatus may be provided in part of the outer circumferential member.

In the body-insertable apparatus, the storage chamber may have an outer wall formed by the balloon member to store the predetermined fluid in a space region covered by an inner surface of the storage chamber.

In the body-insertable apparatus, the balloon member may be arranged so that at least part of an outer surface of the balloon member is contacted with an outer space of the body-insertable apparatus to change the volume of the body-insertable apparatus with changes in the volume of an inner space of the balloon member.

A method for manufacturing a body-insertable apparatus according to another aspect of the present invention, where the body-insertable apparatus is introduced into a body and performs at least one of taking in and discharging predetermined fluid in the body based on changes in the internal volume of a predetermined balloon member with at least one of expanding and contracting by the balloon member, includes forming an extraction and contraction film made of elastic material on a surface of a communication pipe forming part, the surface including an opening communicated with a predetermined communication pipe; and forming the balloon member by contacting and fixing an outer circumferential portion of the expansion and contraction film onto the communication pipe forming part.

According to this method, since the balloon member is formed by forming the extraction and contraction film on the predetermined communication pipe forming part and then contacting and fixing an outer circumferential portion of the formed expansion and contraction film onto the communication pipe forming part, the balloon member as being a flow generating unit can be formed easily.

In the method, the forming the extraction and contraction film may include arranging a film-like member formed of predetermined elastic material on the surface including the opening of the communication pipe forming part.

In the method, the forming the extraction and contraction film may include coating a liquefied elastic material onto the surface including the opening of the communication pipe forming part to solidify the liquefied elastic material again.

The method may further include liquefying an elastic material by heating, and the forming the extraction and contraction film may include coating the liquefied elastic material onto the surface including the opening of the communication pipe forming part to solidify the liquefied elastic material again.

The method may further include coating a protective film onto part of the surface including the opening of the communication pipe forming part, and the forming the extraction and contraction film may include coating the liquefied elastic material onto the surface that covers the protective film and that includes the opening of the communication pipe forming part to solidify the liquefied elastic material again.

The method may further include liquefying an elastic material by a solvent, and the forming the extraction and contraction film forming may include coating the liquefied elastic material onto the surface including the opening of the communication pipe forming part to solidify the liquefied elastic material again.

BEST MODE(S) FOR CARRYING OUT THE INVENTION

A body-insertable apparatus according to best mode for embodying the present invention (hereinafter, referred to as an "embodiment") will be described below. The drawings are schematic and it should be noted that the relation between the thickness and width of parts and the thickness proportion between the respective parts are different from actual ones. Parts in which the size relation and proportion between the drawings are different are included.

A body-insertable apparatus according to a first embodiment will be described first. The body-insertable apparatus according to the first embodiment has a flow generating unit for generating a flow state in the direction from the outer space of the body-insertable apparatus toward a storage chamber and has the function of taking in fluid such as body fluid in a predetermined region in a body after being introduced into the body.

Figure 1:
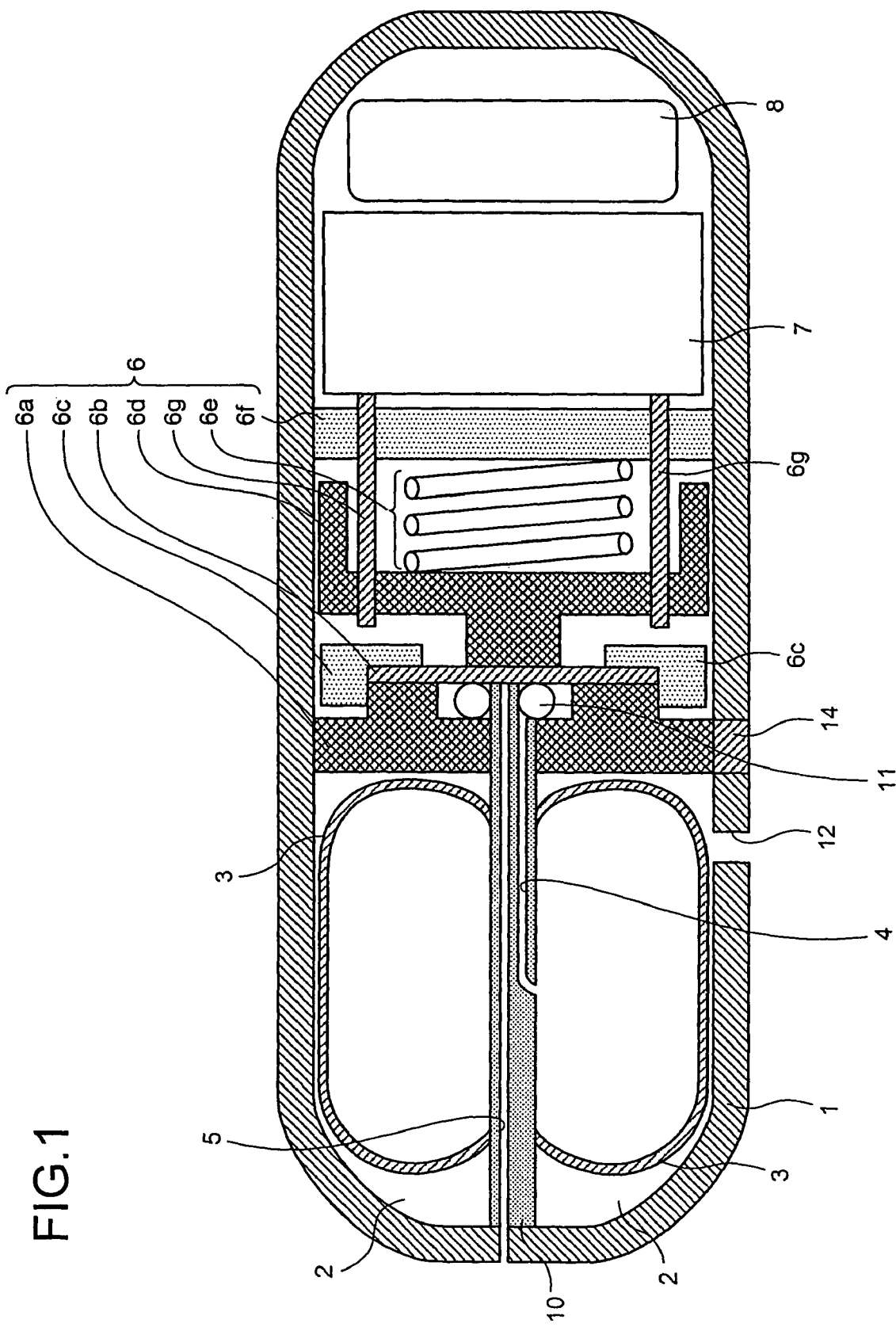
FIG. 1 is a schematic diagram showing the configuration of a body-insertable apparatus according to a first embodiment.

FIG. 1 is a schematic cross-sectional view showing the configuration of a body-insertable apparatus according to the first embodiment. As shown in FIG. 1, the body-insertable apparatus according to the first embodiment has, in a housing 1 defining an outside shape, a storage chamber 2 storing the taken body fluid, a balloon member 3 forming part of the outer wall portion of the storage chamber 2 and changing the volume of the storage chamber 2, and a first communication pipe 4 and a second communication pipe 5 functioning as paths when communicating the inside of the balloon member 3 with the outside of the body-insertable apparatus. The body-insertable apparatus according to the first embodiment also has a communication adjusting mechanism 6 adjusting the communication state between the first communication pipe 4 and the second communication pipe 5, a control circuit 7 controlling the driving state of the communication adjusting mechanism 6, and a power source part 8 supplying a driving power to the control circuit 7.

The first communication pipe 4 and the second communication pipe 5 have the function of communicating the outside (hereinafter, simply called an "outer space") of the body-insertable apparatus according to the first embodiment with the inside of the balloon member 3. The first communication pipe 4 and the second communication pipe 5 are formed in a communication pipe forming part 10 having a bar-like configuration extended along the center axis in the longitudinal direction of the body-insertable apparatus according to the first embodiment. One end of the first communication pipe 4 is opened to the inner space of the balloon member 3 and one end of the second communication pipe 5 is opened to the outer space. The communication state between the other end of the first communication pipe 4 and the other end of the second communication pipe 5 is adjusted by the communication adjusting mechanism 6. Specifically, the other end of the first communication pipe 4 and the other end of the second communication pipe 5 are opened to the concave region of a sheet holding substrate 6a (described later). The communication state between the other end of the first communication pipe 4 and the other end of the second communication pipe 5 is adjusted according to the shape change of a sheet member 6b (described later) covering such concave region.

The communication adjusting mechanism 6 adjusts the communication state between the first communication pipe 4 and the second communication pipe 5 according to control of the control circuit 7 and has the function of controlling expanding and contracting operation of the balloon member 3 as the flow generating part by performing such adjusting operation. Specifically, the communication adjusting mechanism 6 has the sheet holding substrate 6a formed with a predetermined concave region, a sheet member 6b arranged to cover the concave region on the sheet holding substrate 6a, and a fixing member 6c contacting and fixing the outer circumferential portion of the sheet member 6b onto the sheet holding substrate 6a. The communication adjusting mechanism 6 also has a pressing member 6d for applying a predetermined press force to the sheet member 6b, a spring member 6e for generating the press force applied by the pressing member 6d, a spring substrate 6f holding the spring member 6e, and a shape memory member 6g for changing the position of the pressing member 6d to the sheet member 6b.

The sheet holding substrate 6a has a configuration in which the concave region is formed in the region corresponding to the communication pipe forming part 10. Specifically, the concave region is formed near the center axis in the longitudinal direction of the body-insertable apparatus formed with the communication pipe forming part 10 so that the end of the first communication pipe 4 and the end of the second communication pipe 5 formed in the communication pipe forming part 10 are opened into such concave region.

The sheet member 6b directly controls the communication state between the first communication pipe 4 and the second communication pipe 5. Specifically, the sheet member 6b is formed of a watertight and flexible material such as a silicon sheet, is arranged on the sheet holding substrate 6a to cover the concave region formed in the sheet holding substrate 6a, and is fixed by the fixing member 6c in the state that the outer circumferential portion thereof is contacted with the sheet holding substrate 6a. The sheet member 6b has the function of closing the opening of the second communication pipe 5 by being maintained to be contacted with the end of the second communication pipe 5 upon application of the predetermined press force by the pressing member 6d to block the communication state between the first communication pipe 4 and the second communication pipe 5. When the press force by the pressing member 6d is lowered, the sheet member 6b whose shape is changed, as described later, is moved away from the end of the second communication pipe 5 and communicates the first communication pipe 4 with the second communication pipe 5. To assist such function of the sheet member 6b, an O ring 11 is arranged in the concave region of the sheet holding substrate 6a or near the region formed with the first communication pipe 4 and the second communication pipe 5.

The fixing member 6c fixes the sheet member 6b onto the sheet holding substrate 6a. Specifically, the fixing member 6c has the function of contacting and fixing the outer circumferential portion of the sheet member 6b onto the sheet holding substrate 6a by applying the press force to the sheet holding substrate 6a side of the outer circumferential portion of the sheet member 6b. The fixing member 6c fixes the sheet member 6b in such form. The center portion of the sheet member 6b (in FIG. 1, the region near the center axis in the longitudinal direction of the body-insertable apparatus, more specifically, the region corresponding to the position of the opening of the second communication pipe 5) freely changes the shape according to the press force of the pressing member 6d and prevents fluid (described later) flowed into the concave region of the sheet holding substrate 6a through the first communication pipe 4 from being leaked into the region other than the second communication pipe 5.

The spring member 6e generates the press force the pressing member 6d applies to the sheet member 6b. Specifically, the spring member 6e has one end fixed onto the spring substrate 6f and the other end fixed onto the pressing member 6d so that the spring length is maintained to be shorter than the natural length and has the function of exerting a resilient force in the direction in which the sheet member 6b is positioned with respect to the pressing member 6d (the left direction in FIG. 1).

The shape memory member 6g changes the position of the pressing member 6d with respect to the sheet member 6b. Specifically, the shape memory member 6g has a bar-like or coil-like configuration in which one end is fixed onto the spring substrate 6f and the other end is fixed onto the pressing member 6d and is formed of a shape memory alloy having a predetermined shape memory characteristic and a predetermined electric resistance value. More specifically, the shape memory member 6g has a length enough for contacting the pressing member 6d with the sheet member 6b under the temperature conditions equal to the temperature in a body. The shape memory member 6g has the function of changing its shape at a predetermined temperature, e.g., under the temperature conditions sufficiently higher than the temperature in a body to move the pressing member 6d away from the sheet member 6b.

The control circuit 7 has the function of controlling driving as the flow generating unit of the balloon member 3 through the presence or absence of electric current supply to the shape memory member 6g and functions as an example of a control unit controlling expanding and contracting operations of an expansion and contraction film changing the shape by performing at least one of the expanding and contracting operations. Specifically, the control circuit 7 has the function of supplying an electric current to the shape memory member 6g when the body-insertable apparatus according to the first embodiment is introduced into the body to reach a predetermined position in the body. Such electric current is flowed into the shape memory member 6g to generate Joule heat in the shape memory member 6g so that the temperature of the shape memory member 6g rises due to the Joule heat to change the shape of the shape memory member 6g. A configuration defining the electric current supply timing may have a timer mechanism or may incorporate a radio reception mechanism and supply a control signal from the outside. It may also have a sensor (such as a lead switch) sensing magnetism to turn on the circuit so that the circuit is turned on by a magnetic field applied from the outside of the body for supplying an electric current to the shape memory alloy.

The balloon member 3 functions as an example of the flow generating unit generating a flow state of predetermined fluid. Specifically, the balloon member 3 has the expansion and contraction film whose shape is changed with the contracting operation and has the function of generating a flow state of peripheral fluid with the shape change of the expansion and contraction film.

More specifically, the balloon member 3 is formed by the expansion and contraction film formed of an elastic material such as rubber. A predetermined amount of fluid (e.g., physiological salt solution) is injected into the inside of the balloon member 3 to maintain the expansion and contraction film to be extended. As described later, control of the control circuit 7 communicates the inner space of the balloon member 3 with the outer space of the body-insertable apparatus. The balloon member 3 has the function of generating a flow state of fluid such as body fluid in the direction from the outer space to the inner space when the expansion and contraction film starts the contracting operation to generate a negative pressure in the inner space of the storage chamber 2. In the present invention, the "balloon member" refers to a general configuration having the function of holding fluid inside and covering at least part of the space region holding the fluid by the expansion and contraction film and is not limited to the configuration covering the entire space region holding the fluid by the expansion and contraction film.

The storage chamber 2 stores the taken body fluid. Specifically, the storage chamber 2 is formed of the balloon member 3 and an outer circumferential member arranged in the position opposite the outer surface of the balloon member 3 to be spaced from the outer surface of the balloon member 3 by a predetermined distance. As shown in FIG. 1, the back surface of the sheet holding substrate 6a (the surface opposite the surface arranged with the sheet member 6b), the surface of the communication pipe forming part 10, and part of the inner surface of the housing 1 correspond to the outer circumferential member according the first embodiment.

An inlet 12 is formed in part of the outer circumferential member according to the first embodiment or part of the housing 1 of the example of FIG. 1 as an opening for suction of body fluid into the storage chamber 2. In this case, the inlet 12 functions as an opening communicating the space region as the storage chamber 2 with the outer space of the body-insertable apparatus. A weighting member 14 formed of a member having a predetermined weight is arranged near the inlet 12 to always open the inlet 12 in the body vertically downward.

Figure 2:
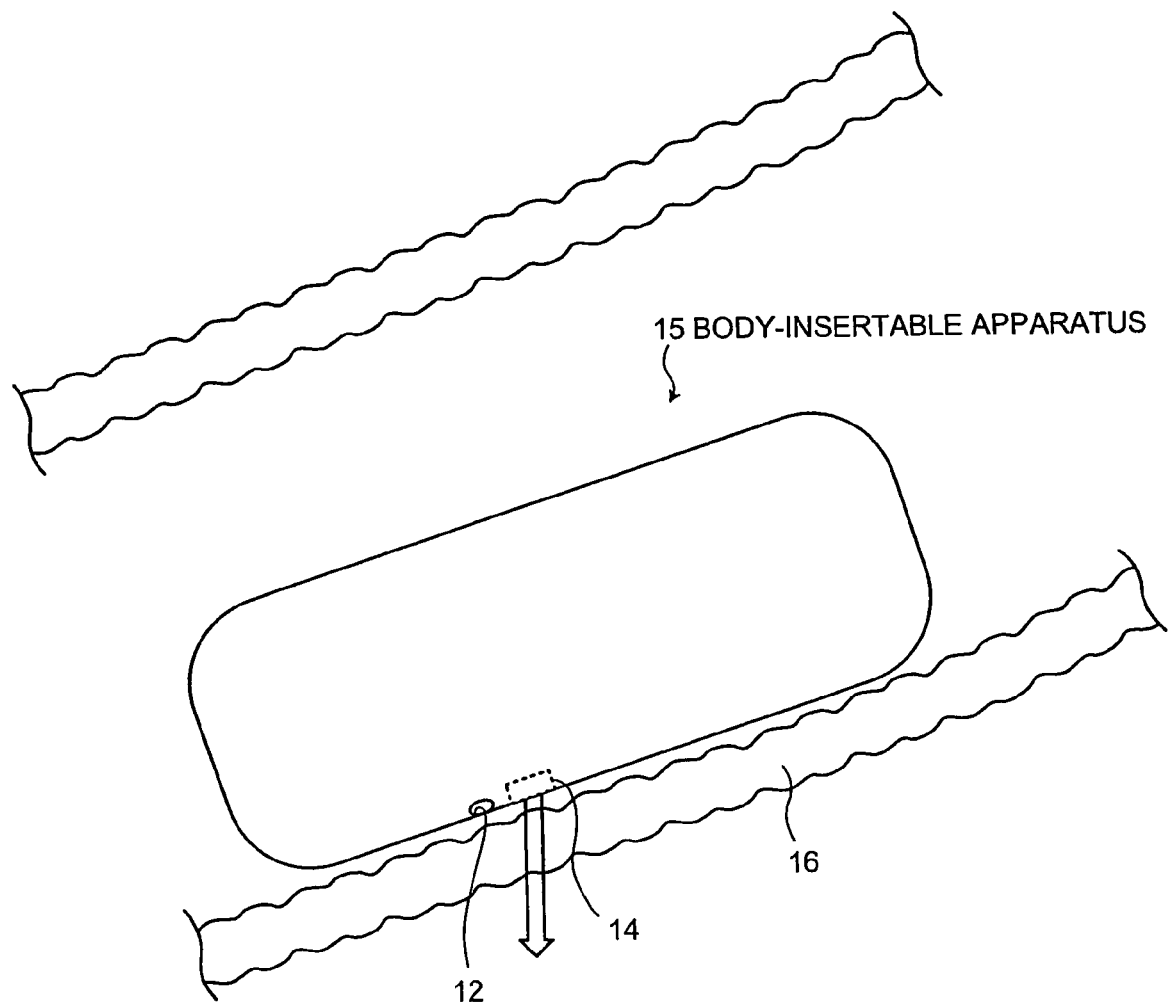
FIG. 2 is a schematic diagram showing the state in a body of the body-insertable apparatus.

FIG. 2 is a schematic diagram showing an embodiment when the body-insertable apparatus according to the first embodiment is introduced into the body. As described above, a body-insertable apparatus 15 performs the function of taking in fluid such as body fluid or the like when sequentially moving in a digestive organ 16 such as a mouse, a gullet, a stomach, a small intestine, or a large intestine of the body to reach a predetermined portion. From the viewpoint of taking in body fluid, the inlet 12 is preferably positioned near the inner surface of the digestive organ 16 in which a sufficient amount of body fluid exists.

In view of such viewpoints, according to the first embodiment, the weighting member 14 is arranged near the inlet 12 so that the inlet 12 is opened near the inner surface of the digestive organ 16 in the body. As shown in FIG. 2, the body-insertable apparatus 15 is moved in contact with the region positioned vertically downward in the inner surface of the digestive organ 16 in the body. In order that the inlet 12 is positioned near the inner surface of the digestive organ 16 in the body, the inlet 12 is preferably opened vertically downward. The first embodiment employs a configuration in which the weighting member 14 is arranged near the inlet 12 to open the inlet 12 in the body vertically downward. In such configuration, the body-insertable apparatus according to the first embodiment can efficiently take in body fluid. The configuration in which the inlet 12 is opened in the body vertically downward may adjust the position of each component arranged in the housing 1 in addition to provision of the weighting member 14. When each component is arranged so that the center-of-gravity position of the body-insertable apparatus is positioned near the inlet 12, the inlet 12 can be opened vertically downward.

The operation of the body-insertable apparatus according to the first embodiment will be described. As described previously, the body-insertable apparatus according to the first embodiment is introduced into the body to take in fluid such as body fluid. The fluid taking will be described below.

Figure 3:
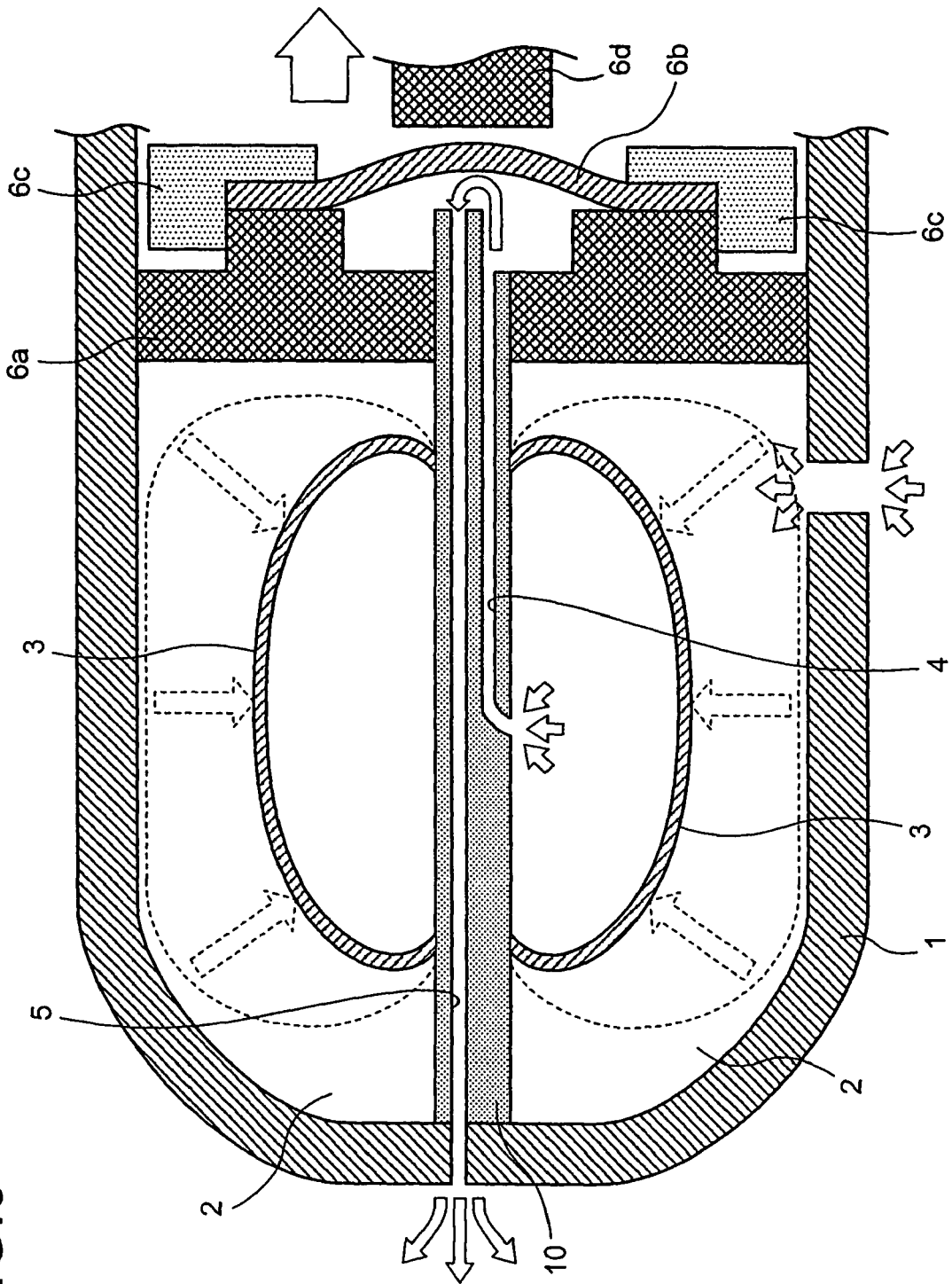
FIG. 3 is a schematic diagram for explaining the operation of the body-insertable apparatus.

FIG. 3 is a schematic diagram for explaining the fluid taking of the body-insertable apparatus according to the first embodiment. According to the first embodiment, part of the storage chamber 2 is formed of the balloon member 3 as the extraction and contraction film. The contracting operation of the balloon member 3 generates a flow state of fluid existing in the outside of the body-insertable apparatus to perform suction of the fluid of the outside into the storage chamber 2 based on the generated flow state. Such operation of the body-insertable apparatus will be described with reference to FIG. 3.

The control circuit 7 supplies a predetermined electric current to the shape memory member 6g. The temperature of the shape memory member 6g rises by Joule heat generated with the electric current to shape its change. Specifically, the shape memory member 6g is formed in a bar shape and is previously formed so that the longitudinal length is contracted at high temperature and changes its shape so that the longitudinal length is shortened with temperature rise due to the Joule heat. The pressing member 6d fixed onto one end of the shape memory member 6g is moved in the direction moved away from the sheet member 6b as shown in FIG. 3 (the right direction in FIG. 3) as the longitudinal length of the shape memory member 6g is contracted so that the press force to the sheet member 6b is reduced or 0.

The press force to the sheet member 6b is reduced to eliminate the contact state between the sheet member 6b and the second communication pipe 5. The end of the first communication pipe 4 is communicated with the end of the second communication pipe 5 via the concave region formed in the sheet holding substrate 6a. As described above, the first communication pipe 4 is formed to be communicated with the inner space of the balloon member 3 and the second communication pipe 5 is formed to be communicated with the outer space of the body-insertable apparatus. The first communication pipe 4 is communicated with the second communication pipe 5 so as to communicate the inner space of the balloon member 3 with the outer space of the body-insertable apparatus.

The inner space of the balloon member 3 is communicated with the outer space of the body-insertable apparatus to start the contracting operation of the expansion and contraction film forming the balloon member 3. Specifically, the balloon member 3 discharges fluid held in the inner space through the first communication pipe 4 and the second communication pipe 5 into the outer space by the contracting operation of the expansion and contraction film to reduce the volume of the inner space of the balloon member 3.

According to the first embodiment, the storage chamber 2 is formed of the balloon member 3 and the outer circumferential member. The volume of the region covered by the outer surface of the balloon member 3 and the inner surface of the outer circumferential member is increased by the reduced volume of the inner space of the balloon member 3 to form a negative pressure in the storage chamber 2. Based on such negative pressure, a flow state from the outer space toward the storage chamber 2 with respect to fluid such as body fluid in the outer space is generated. The body fluid or the like of a body flows from the outer space of the body-insertable apparatus into the storage chamber 2 according to the flow state to perform the taking operation.

Figure 4:
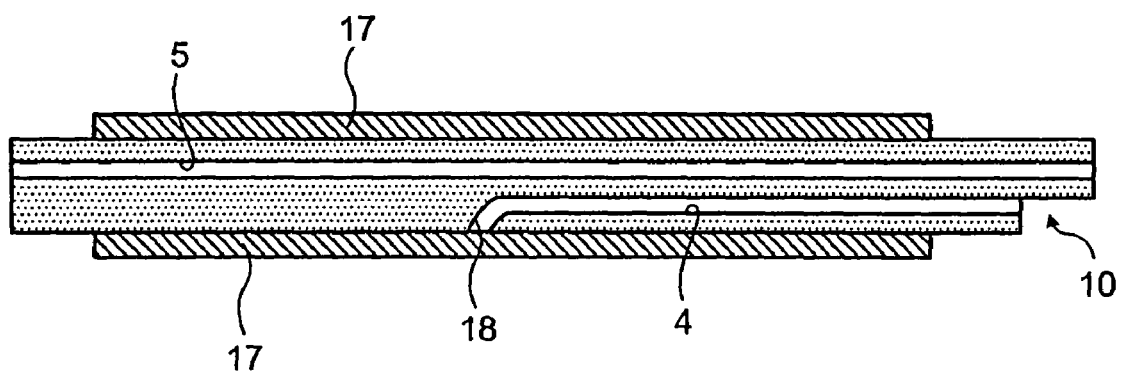
FIG. 4 is a schematic diagram showing part of a manufacturing process of the body-insertable apparatus.
Figure 5:
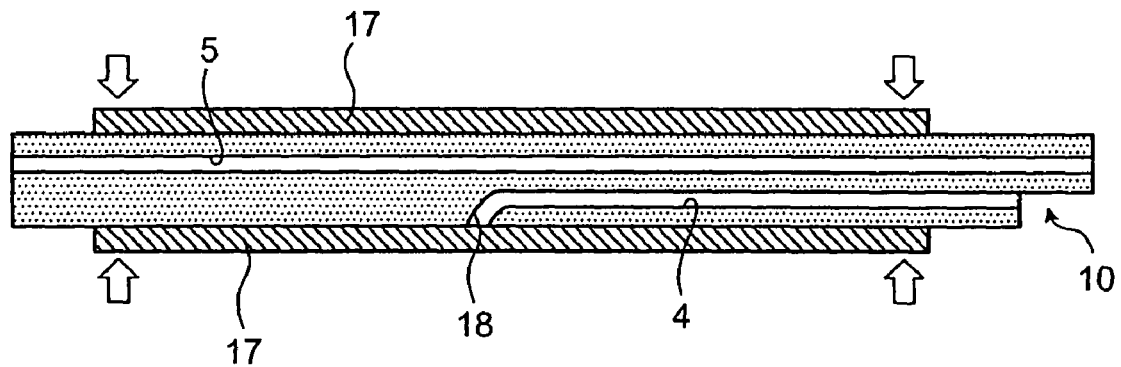
FIG. 5 is a schematic diagram showing part of the manufacturing process of the body-insertable apparatus.

A method of manufacturing the body-insertable apparatus according to the first embodiment will be described. FIGS. 4 and 5 are schematic diagrams for explaining part of the manufacturing process of the body-insertable apparatus. As shown in FIGS. 4 and 5, according to the first embodiment, a method for forming the balloon member 3 as a component significantly different from the conventional one will be focusably described below.

As shown in FIG. 4, an expansion and contraction film 17 formed of an elastic material such as rubber or the like is arranged on the surface of the communication pipe forming part 10 formed with the first communication pipe 4 and the second communication pipe 5. The expansion and contraction film 17 is arranged to cover an opening 18 communicated with at least the first communication pipe 4 to form the balloon member 3. The communication state between the inner space of the formed balloon member 3 and the first communication pipe 4 is secured. FIG. 4 (and FIG. 5) shows a cross-sectional configuration for facilitating understanding. The expansion and contraction film 17 is arranged to be in a cylindrical shape covering the entire side of the communication pipe forming part 10 actually formed in a bar shape.

The space region between the expansion and contraction film 17 and the communication pipe forming part 10 is blocked from other regions. Specifically, as shown in FIG. 5, the outer circumferential portion of the expansion and contraction film 17 arranged on the surface of the communication pipe forming part 10 is contacted and fixed onto the communication pipe forming part 10. As a specific embodiment of the contacting and fixing process, the outer circumferential portion of the expansion and contraction film 17 is subject to a thermocompression process. The contacting and fixing process can be performed by coating an adhesive onto the region corresponding to the outer circumferential portion of the surface of the communication pipe forming part 10. The surface of the communication pipe forming part 10 formed with the balloon member 3 on its surface, the communication adjusting mechanism 6, the control circuit 7, and the power source part 8 are incorporated into the housing 1, thereby manufacturing the body-insertable apparatus according to the first embodiment.

In forming the balloon member 3, it is effective to form the expansion and contraction film 17 by coating a liquefied elastic material onto the communication pipe forming part 10 to solidify it. The elastic material forming the expansion and contraction film 17 is formed of a predetermined resin. Such resin is previously heated to be liquefied (the elastic material liquefying process). The liquefied elastic material is coated onto a predetermined region on the surface of the communication pipe forming part 10 to form the expansion and contraction film 17. There are a case that the melting point of the elastic material forming the expansion and contraction film 17 is lower than the melting point of the material forming the communication pipe forming part 10 and a case that the melting point of the elastic material forming the expansion and contraction film 17 is higher than the melting point of the material forming the communication pipe forming part 10. The method for forming the balloon member 3 using the liquefied elastic material will be described by separating the cases.

Figure 6:
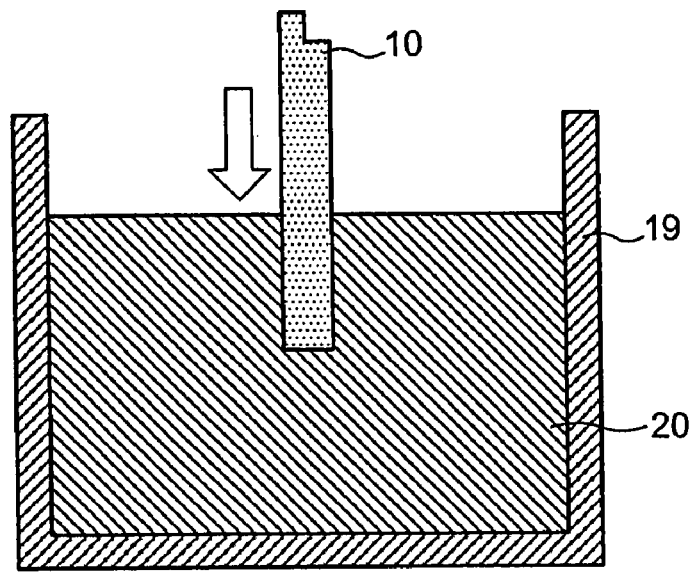
FIG. 6 is a schematic diagram showing part of another manufacturing process of the body-insertable apparatus.

There will be described the case that the melting point of the elastic material forming the expansion and contraction film 17 is lower than the melting point of the material forming the communication pipe forming part 10. FIG. 6 is a schematic diagram for explaining the method for forming the balloon member 3 using the liquefied elastic material in such case. As shown in FIG. 6, an elastic material 20 held in a heat-resistant case 19 is heated at a temperature above its melting point to be liquefied.

As shown in FIG. 6, the communication pipe forming part 10 is immersed into the liquefied elastic material 20 to a depth to some degree to coat the elastic material 20 onto the surface of the communication pipe forming part 10. The communication pipe forming part 10 is pulled up to be gradually cooled to solidify the elastic material 20. The expansion and contraction film 17 is formed on the surface of the communication pipe forming part 10. As shown in FIG. 5, the expansion and contraction film 17 is fixed onto the region corresponding to the outer circumferential portion of the surface of the communication pipe forming part 10 to form the balloon member 3.

There will be described the method for forming the balloon member 3 when the melting point of the elastic material forming the expansion and contraction film 17 is higher than the melting point of the material forming the communication pipe forming part 10. In such case, it should be noted that the surface of the communication pipe forming part 10 can be melted by immersing the communication pipe forming part 10 into the liquefied elastic material 20. Specifically, it is preferable to coat the liquefied elastic material after providing a devise shown in FIG. 7 to the communication pipe forming part 10.

Figure 7:
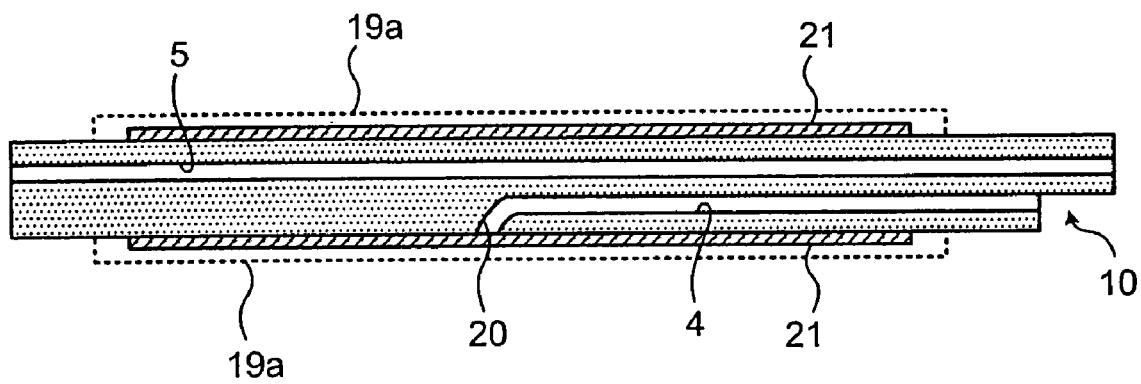
FIG. 7 is a schematic diagram showing part of a further manufacturing process of the body-insertable apparatus.

Before immersing the communication pipe forming part 10 into the liquefied elastic material 20, as shown in FIG. 7, a heat-resistance coating 21 is provided to a predetermined region on the surface of the communication pipe forming part 10. Any material forming the heat-resistant coating 21 can be used and must exhibit a characteristic stable under the temperature conditions of at least about the melting point of the elastic material 20. As shown in FIG. 7, a specific region coated with the heat-resistant coating 21 is a region except for the outer circumferential portion of an expansion and contraction forming region 19a.

The heat-resistant coating 21 functions as a heat-resistant protective film preventing the melting of the surface of the communication pipe forming part 10 due to the heat of the elastic material 20 when the liquefied elastic material 20 is coated onto the communication pipe forming part 10. Specifically, the heat-resistant coating 21 is formed in part of the surface of the communication pipe forming part 10 including the opening 20, e.g., the region except for the outer circumferential portion of the expansion and contraction forming region 19a shown in FIG. 7.

Such heat-resistant coating 21 is coated so that the elastic material 20 is coated onto the surface of the communication pipe forming part 10 covering the heat-resistant coating 21 and including the opening 20 (that is, the expansion and contraction forming region 19a). The surface of the communication pipe forming part 10 is protected when being immersed into the elastic material 20 and the process shown in FIG. 5 need not be performed. The heat-resistant coating 21 is not formed in the outer circumferential portion of the expansion and contraction forming region 17a. In the region corresponding to the outer circumferential portion, the surface of the communication pipe forming part 10 is directly contacted with the elastic material 20. The temperature of the elastic material 20 is above the melting point of the communication pipe forming part 10. The surface of the communication pipe forming part 10 is partially melted in such portion. In the region corresponding to the outer circumferential portion, the surface portion of the communication pipe forming part 10 and the elastic material 20 are contacted with each other to be solidified by gradual cooling after coating the elastic material 20 so that the process shown in FIG. 5 need not be performed.

In the examples shown in FIGS. 6 and 7, an embodiment of liquefying the elastic material is not limited to thermal melting and the elastic material can be melted in a predetermined solvent to be liquefied. In such case, after coating the liquefied elastic material, the solvent is evaporated to form the expansion and contraction film 17.

The advantage of the body-insertable apparatus according to the first embodiment will be described. The body-insertable apparatus according to the first embodiment generates a flow state of fluid such as body fluid or the like by the flow generating unit (the balloon member 3) having the expansion and contraction film in order to taking fluid such as body fluid or the like existing in the outer space of the body-insertable apparatus.

Such configuration having the expansion and contraction film is employed to simplify the configuration of the flow generating unit. Specifically, the first embodiment employs the configuration in which a flow state is directly generated by the shape change of the expansion and contraction film with contraction. Unlike the conventional apparatus, the configuration such as a spring member for generating a flow state is unnecessary so that the configuration can be simplified. According to the configuration of the first embodiment, the shape of the expansion and contraction film having a predetermined surface area is changed to generate a flow state of fluid. The flow generating unit can be constructed of the expansion and contraction film without using the spring member. The body-insertable apparatus using a simple configuration as the flow generating unit can be realized.

The body-insertable apparatus according to the first embodiment employs the configuration in which the communication adjusting mechanism 6 has the spring member 6e. It should be noted that the spring member 6e is different from the spring member of the conventional body-insertable apparatus. The spring member in the conventional body-insertable apparatus changes the volume of the storage chamber and must have the entire length to some degree corresponding to the amount of change of the volume. The spring member 6e according to the first embodiment only generates a press force of the pressing member 6d and can use any configuration having a spring constant exerting a predetermined resilient force. The spring member 6e according to the first embodiment may be sufficiently smaller than that shown in FIG. 1. The reduction in size of the body-insertable apparatus due to the existence of the spring member 6e cannot be prevented.

According to the first embodiment, unlike the conventional apparatus, the movable mechanism generating a flow state is not formed to be independent of the storage chamber. The balloon member 3 as the flow generating unit forms part of the storage chamber 2. By employing such configuration, the body-insertable apparatus according to the first embodiment can simplify its inner configuration as compared with the conventional body-insertable apparatus generating a flow state using the spring member.

The flow generating unit of the body-insertable apparatus according to the first embodiment is formed of the extraction and contraction film having a predetermined surface area. As shown in FIG. 1, the flow generating unit can be diverted as part of the outer wall of the storage chamber. As compared with the conventional body-insertable apparatus which uses the spring member as the flow generating unit formed to be independent of the storage chamber, the body-insertable apparatus according to the first embodiment integrating the flow generating unit with the storage chamber can realize simplification and reducing in size of the configuration.

The body-insertable apparatus according to the first embodiment has a configuration using as the flow generating unit the balloon member 3 generating a flow state by changing the volume of the inner space. As described above, the balloon member 3 has the function of generating a flow state by reducing the volume of the inside based on control of the control circuit 7. As taking in fluid such as body fluid proceeds, the occupied area of the balloon member 3 in the body-insertable apparatus is significantly reduced.

The balloon member 3 can be previously formed so that the extraction and contraction film forming the balloon member 3 is contacted with the communication pipe forming part 10 when the fluid (such as a physiological salt solution) of the inside is completely discharged. In such case, the occupied volume of the balloon member 3 in the body-insertable apparatus is almost 0 after completing the taking. Body fluid in an amount almost equal to the occupied volume of the balloon member 3 before starting the taking can be taken in. The body-insertable apparatus according to the first embodiment can efficiently use the inner space and can take in a large amount of fluid.

The body-insertable apparatus according to the first embodiment can be easily manufactured. As shown in FIGS. 4 and 5, when forming the balloon member 3 in the body-insertable apparatus according to the first embodiment, the extraction and contraction film 17 is arranged on the surface of the communication pipe forming part 10 and the predetermined outer circumferential portion of the extraction and contraction film 17 is contacted with the communication pipe forming part 10 to form the balloon member 3. The body-insertable apparatus according to the first embodiment can be easily manufactured as compared with that using the spring member as the flow generating unit.

A body-insertable apparatus according to a second embodiment will be described. The body-insertable apparatus according to the second embodiment taking in fluid such as body fluid like the first embodiment and employs a configuration controlling the extracting and contracting operation of the balloon member as the flow generating unit by controlling the communication state between the storage chamber and the outer space. In the below description, components indicated by the same names and symbols as the first embodiment have the same configurations and functions as the first embodiment unless otherwise specified. This is the same in the later-described third and fourth embodiments.

Figure 8:
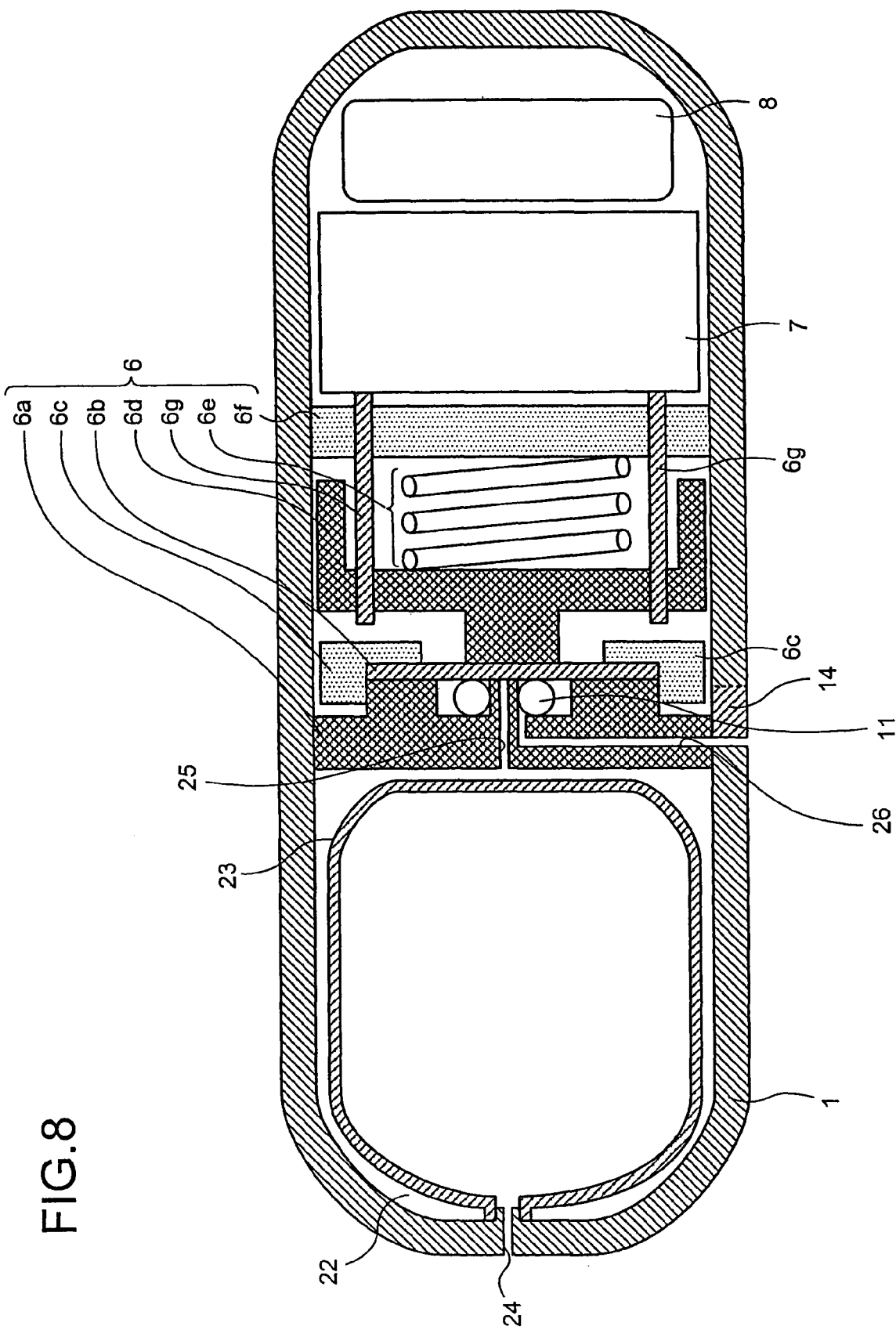
FIG. 8 is a schematic diagram showing the configuration of a body-insertable apparatus according to a second embodiment.

FIG. 8 is a schematic diagram showing the configuration of the body-insertable apparatus according to the second embodiment. As shown in FIG. 8, the body-insertable apparatus according to the second embodiment has the housing 1, the communication adjusting mechanism 6, the control circuit 7, and the power source circuit 8 having the same configuration as the first embodiment and has a configuration different from the body-insertable apparatus according to the first embodiment with respect to the configuration of the balloon member, the storage chamber in which the balloon member is part of the outer wall portion, and the communication mechanism between the components and the outer space.

Specifically, as shown in FIG. 8, the body-insertable apparatus according to the second embodiment has, in the housing 1, a storage chamber 22 for storing the taken fluid such as body fluid, a balloon member 23 forming part of the outer wall portion of the storage chamber 22 to change the volume of the storage chamber 22, an outlet 24 communicating the balloon member 23 with the outside of the body-insertable apparatus, a first communication pipe 25 communicated with the storage chamber 22, and a second communication pipe 26 communicated with the outside of the body-insertable apparatus. The first communication pipe 25 and the second communication pipe 26 are formed in the sheet holding substrate 6a. Like the first communication pipe 4 and the second communication pipe 5 according to the first embodiment, the first communication pipe 25 and the second communication pipe 26 are formed so that one end of the first communication pipe 25 and one end of the second communication pipe 26 are formed to be opened in the concave region formed in the sheet holding substrate 6a.

According to the second embodiment, the balloon member 23 holds fluid such as a physiological salt solution like the first embodiment and maintains the balloon member to be communicated with the outer space of the body-insertable apparatus via the outlet 24 before and after taking in fluid such as body fluid. The second embodiment employs a configuration in which the first communication pipe 25 and the second communication pipe 26 are arranged between the storage chamber 22 and the outer space of the body-insertable apparatus and the communication state between the first communication pipe 25 and the second communication pipe 26 is controlled by the communication adjusting mechanism 6.

The storage chamber 22 stores the taken fluid such as body fluid like the storage chamber 2 according to the first embodiment. Like the first embodiment, part of the outer wall portion of the storage chamber 22 is formed of the balloon member 23 and specifically, has a configuration storing fluid between the outer surface of the balloon member 23 and the inner surface of the outer circumferential member of the housing 1. The communication state between the inside of the storage chamber 22 and the outside of the body-insertable apparatus is blocked by the sheet member 6b before taking in body fluid. The inside of the storage chamber 22 is maintained to be sealed to prevent the extraction and contraction film constructing the balloon member 23 from being contracted before extraction.

The taking of fluid such as body fluid by the body-insertable apparatus according to the second embodiment will be described briefly. According to the second embodiment, like the first embodiment, the control circuit 7 supplies an electric current to the shape memory member 6g, the temperature of the shape memory member 6g rises by Joule heat due to the electric current, and the shape is changed to contract the longitudinal length. Corresponding to the shape change of the shape memory member 6g, the pressing member 6d is moved away from the sheet member 6b. The state that the sheet member 6b is contacted with the first communication pipe 25 is released. The openings of the first communication pipe 25 and the second communication pipe 26 formed in the concave region of the sheet holding substrate 6a communicate with each other via the concave region. The inside of the storage chamber 22 is communicated with the outer space of the body-insertable apparatus. The volume in the balloon member 23 is decreased by the contracting operation of the extraction and contraction film. The volume of the storage chamber 22 is increased to form a negative pressure in the inner space of the storage chamber 22. The body fluid of the outer space is flowed via the second communication pipe 26 into the storage chamber 22 for taking in body fluid.

The advantage of the body-insertable apparatus according to the second embodiment will be described. Like the first embodiment, the body-insertable apparatus according to the second embodiment has the balloon member 23 in which at least part thereof is formed as the flow generating unit by the extraction and contraction film. The body-insertable apparatus according to the second embodiment has the same advantage as the first embodiment in that the inner configuration can be simplified. Unlike the first embodiment, the body-insertable apparatus according to the second embodiment employs a configuration maintaining the state that the inner space of the balloon member 23 is communicated with the outer space of the body-insertable apparatus and controlling the communication state between the storage chamber 22 and the outer space. As is apparent from the above description, the problem that the body-insertable apparatus according to the second embodiment cannot have the advantage of the first embodiment due to the difference of such configuration cannot arise.

The body-insertable apparatus according to the second embodiment has a configuration in which the first communication pipe 25 and the second communication pipe 26 are formed in the sheet holding substrate 6a. According to the second embodiment, the communication pipe forming part need not be provided so that the inner configuration of the body-insertable apparatus can be further simplified. The volume of the storage chamber 22 can be increased.

A body-insertable apparatus according to a third embodiment will be described. The body-insertable apparatus according to the third embodiment has a configuration storing fluid such as medication in the storage chamber and has the function in which the flow generating unit generates a flow state in the direction from the storage chamber toward the outer space upon reaching a predetermined position in the body, thereby discharging the stored fluid in the body.

Figure 9:
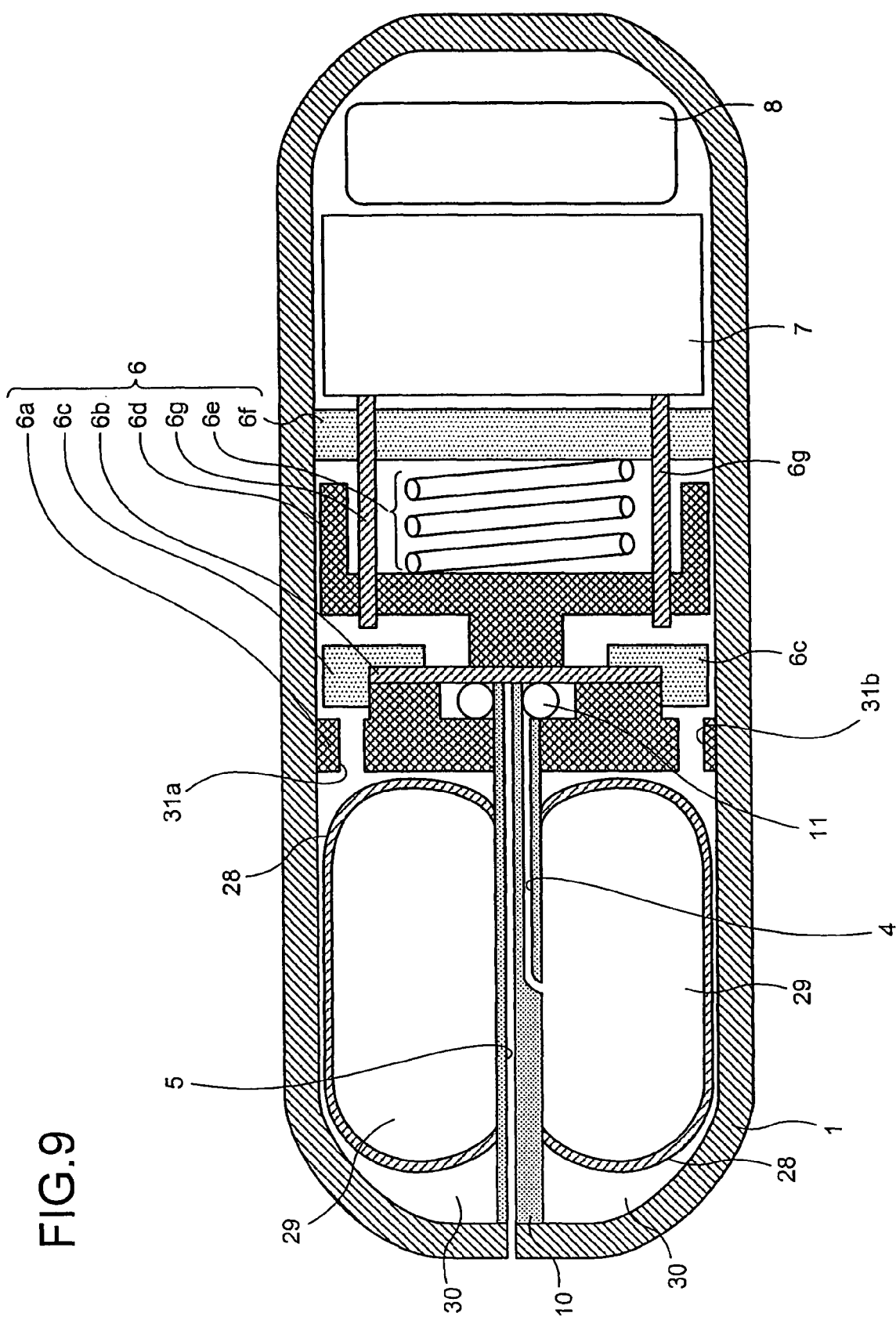
FIG. 9 is a schematic diagram showing the configuration of a body-insertable apparatus according to a third embodiment.

FIG. 9 is a schematic diagram showing the configuration of the body-insertable apparatus according to the third embodiment. As shown in FIG. 9, the body-insertable apparatus according to the third embodiment has basically the same configuration as the body-insertable apparatus according to the first embodiment and has a balloon member 28 having the same configuration as that of the balloon member 3 according to the first embodiment, and a storage chamber 29 storing fluid in a region covered by the inner surface of the balloon member 28. The third embodiment has a configuration in which most part of the outer wall portion of the storage chamber 29 is formed by the balloon member 28 and fluid such as medication discharged in the body is stored in the space region covered by the inner surface of the balloon member 28 (and part of the outer surface of the communication pipe forming part 10).

As described above, the body-insertable apparatus according to the third embodiment discharges fluid such as medication held in the storage chamber 29 in the body. The body-insertable apparatus according to the third embodiment is not formed with an opening such as the inlet 12 shown in the first embodiment and is not provided with the weighting member 14 for positioning the inlet 12 near the inner wall of the digestive organ in the body.

The body-insertable apparatus according to the third embodiment has vents 31a and 31b as openings formed to be extended through part of the sheet holding substrate 6a. According to the third embodiment, corresponding to the omission of the inlet 12, a void region 30 (the region functioning as the storage chamber 2 storing body fluid taken in the first embodiment) is blocked from the outer space of the body-insertable apparatus. With increase in the volume of the void region 30 due to the contracting operation of the balloon member 28 when discharging the fluid, a negative pressure can be formed in the void region 30 to interrupt the contracting operation of the balloon member 28. The third embodiment has a configuration in which the vents 31a and 31b are formed in the sheet holding substrate 6a contacted with the void region 30 (that is, part of the outer circumferential member forming the void region 30). The void region 30 is communicated with other inner space of the housing 1 via the vents 31a and 31b. The formation of the negative pressure in the void region 30 is prevented to prevent the interruption of the contracting operation of the balloon member 28.

The fluid discharging of the body-insertable apparatus according to the third embodiment will be described briefly. The control circuit 7 outputs a predetermined electric current to change the shape of the shape memory member 6g so that the press force of the pressing member 6d given to the sheet member 6b is reduced or 0. This communicates the first communication pipe 4 with the second communication pipe 5. The inner space of the balloon member 28, that is, the inside of the storage chamber 29 is communicated with the outer space of the body-insertable apparatus. The contracting operation of the expansion and contraction film forming the balloon member 28 discharges the fluid such as medication stored in the storage chamber 29 from the body-insertable apparatus via the first communication pipe 4 and the second communication pipe 5. The expansion and contraction film forming the balloon member 28 is contracted to increase the volume of the void region 30. As described above, since the fluid is flowed from other regions via the vents 31a and 31b, the formation of a negative pressure of the void region 30 can be prevented according to the third embodiment.

Using almost the same configuration as the body-insertable apparatus according to the first embodiment, the body-insertable apparatus which discharges fluid stored in the storage chamber. The body-insertable apparatus according to the third embodiment has the advantage of the body-insertable apparatus according to the first embodiment and can discharge fluid such as medication.

As is easily understood by the comparison of the first and third embodiments, the body-insertable apparatus according to the first embodiment is combined with the body-insertable apparatus according to the third embodiment to realize a body-insertable apparatus which has both the function of taking in fluid such as body fluid and the function of discharging fluid such as medication. Specifically, according to the first embodiment, such body-insertable apparatus can be realized by changing fluid held in the inner space of the balloon member 3 from a physiological salt solution to medication.

A modification of the body-insertable apparatus according to the third embodiment will be described. This modification has a configuration in which the void region 30 is communicated with the outer space of the body-insertable apparatus. When the balloon member 28 as the flow generating unit is contracted to increase the volume of the void region 30, fluid existing in the outer space is flowed into the void region 30 to prevent a negative pressure from being formed.

Figure 10:
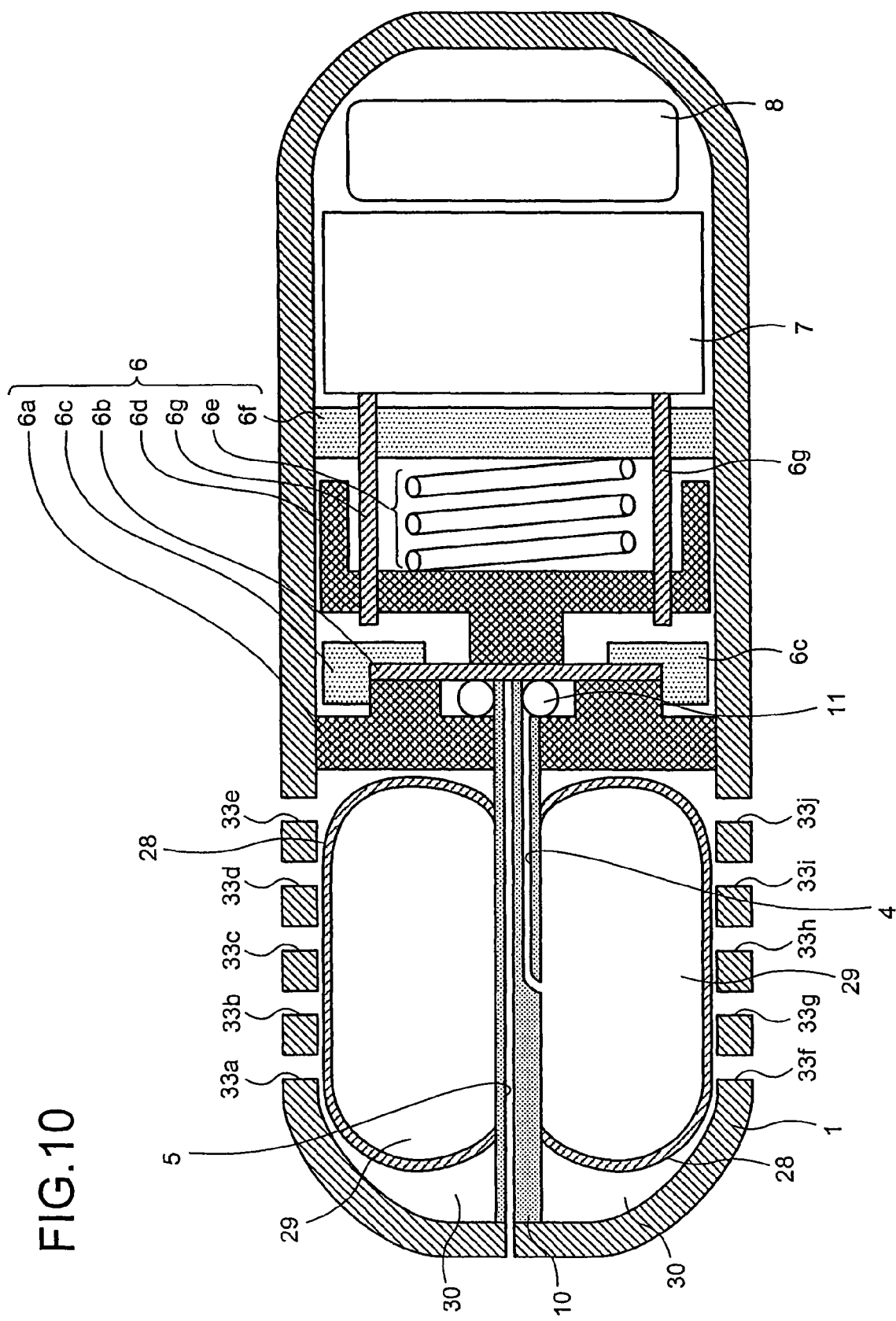
FIG. 10 is a schematic diagram showing the configuration of a body-insertable apparatus according to a modification.

FIG. 10 is a schematic diagram showing the configuration of the body-insertable apparatus according to this modification. As shown in FIG. 10, the body-insertable apparatus according to this modification has basically the same configuration of the third embodiment and has vents 33a to 33j as openings communicated with the outer space of the body-insertable apparatus, in place of the vents 31a and 31b for communicating with other space in the body-insertable apparatus. The vents 33a to 33j are formed in positions corresponding to the position of the void region 30 of the housing 1 as part of the outer circumferential member forming the void region 30. The void region 30 is maintained to be communicated via the vents 33a to 33j with the outer space of the body-insertable apparatus.

It is also effective to employ a configuration in which the void region 30 is communicated with the outer space. It can be assumed that an almost unlimited amount of fluid as compared with the volume of the void region 30 exists in the outer space of the body-insertable apparatus. An almost unlimited amount of fluid can be flowed into the void region 30. When the volume of the void region 30 is increased with the contraction of the balloon member 28, a sufficient amount of fluid can be flowed into the void region 30 to maintain a constant pressure. The causing of a force preventing the contracting operation of the balloon member 28 can be prevented more effectively.

Any value of the number of vents communicated with the outer space and the size thereof can be employed in theory. This modification employs a configuration formed with a large number of vents 33a to 33j. Undigested solid substances in addition to body fluid exist in the outer space of the body-insertable apparatus, that is, in the digestive organ of the body. When forming only a single vent, the vent is clogged by the solid substances to block the communication state between the void region 30 and the outer space. This modification has a large number of vents 33a to 33j. Even if some vents are clogged by solid substances, the communication state between the void region 30 and the outer space can be maintained.

A body-insertable apparatus according to a fourth embodiment will be described. Like the third embodiment, the body-insertable apparatus according to the fourth embodiment has the function of discharging fluid such as medication and has a configuration in which the balloon member functioning as the flow generating unit is exposed to the outer space.

Figure 11:
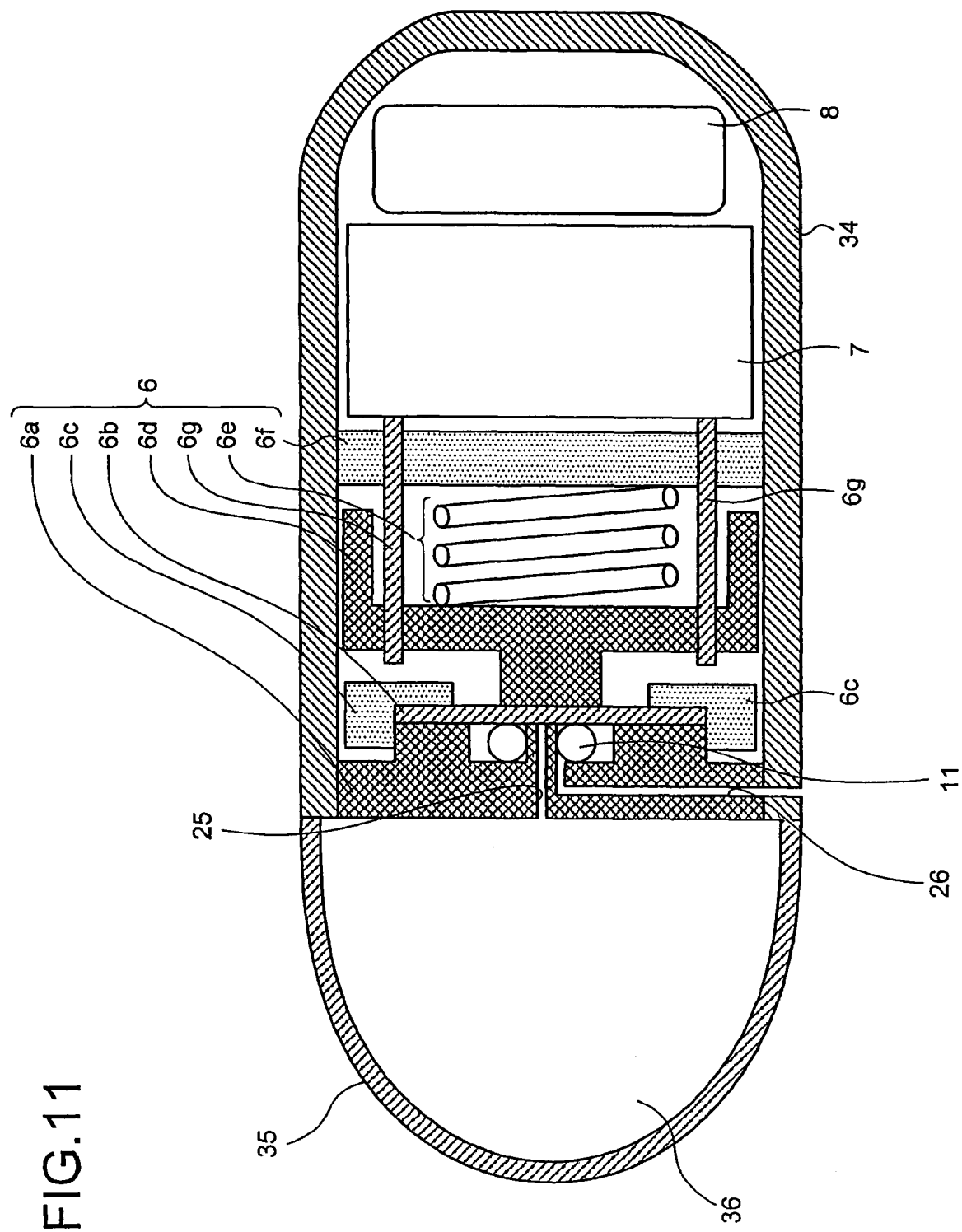
FIG. 11 is a schematic diagram showing the configuration of a body-insertable apparatus according to a fourth embodiment.

FIG. 11 is a schematic diagram showing the configuration of the body-insertable apparatus according to the fourth embodiment. In FIG. 11, components indicated by the same numerals and symbols as the first embodiment have the same configurations and functions as the first embodiment unless otherwise specified.

As shown in FIG. 11, the body-insertable apparatus according to the fourth embodiment has a configuration in which a housing 34 does not include all components and a balloon member 35 functioning as an example of the flow generating unit is directly contacted with the outer space. Specifically, the housing 34 is formed to include only the communication adjusting mechanism 6, the control circuit 7, and the power source part 8 and the balloon member 35 is arranged in the state that the inner space is communicated with the first communication pipe 25 on the outside of the housing 34, more specifically, on the back surface of the sheet holding substrate 6a (a surface opposite the surface on which the sheet member 6b is arranged). Like the third embodiment, the body-insertable apparatus according to the fourth embodiment has a configuration having a storage chamber 36 formed with most part of the outer wall portion by the balloon member 35 and storing fluid such as medication in the storage chamber 36, that is, in a region covered by the balloon member 35 and the back surface of the sheet holding substrate 6a.

The fluid discharging of the body-insertable apparatus according to the fourth embodiment will be described briefly. Like the first embodiment, the control circuit 7 supplies an electric current to the shape memory member 6g at predetermined timing, the temperature of the shape memory member 6g rises by Joule heat due to the electric current to change its shape. The shape change of the shape memory member 6g changes the press force of the pressing member 6d. Corresponding to the change of the press force, the shape change of the sheet member 6b communicates the first communication pipe 25 with the second communication pipe 26. The inside of the storage chamber 36 is communicated with the outer space of the body-insertable apparatus. The stored fluid such as medication is discharged by the contracting operation of the balloon member 35 forming most part of the outer wall of the storage chamber 36.

The advantage of the body-insertable apparatus according to the fourth embodiment will be described. Like the first embodiment, the body-insertable apparatus according to the fourth embodiment has the same advantage as the first embodiment and can reduce, in the body, the occupied volume of the body-insertable apparatus after completing the fluid discharging.

Figure 12:
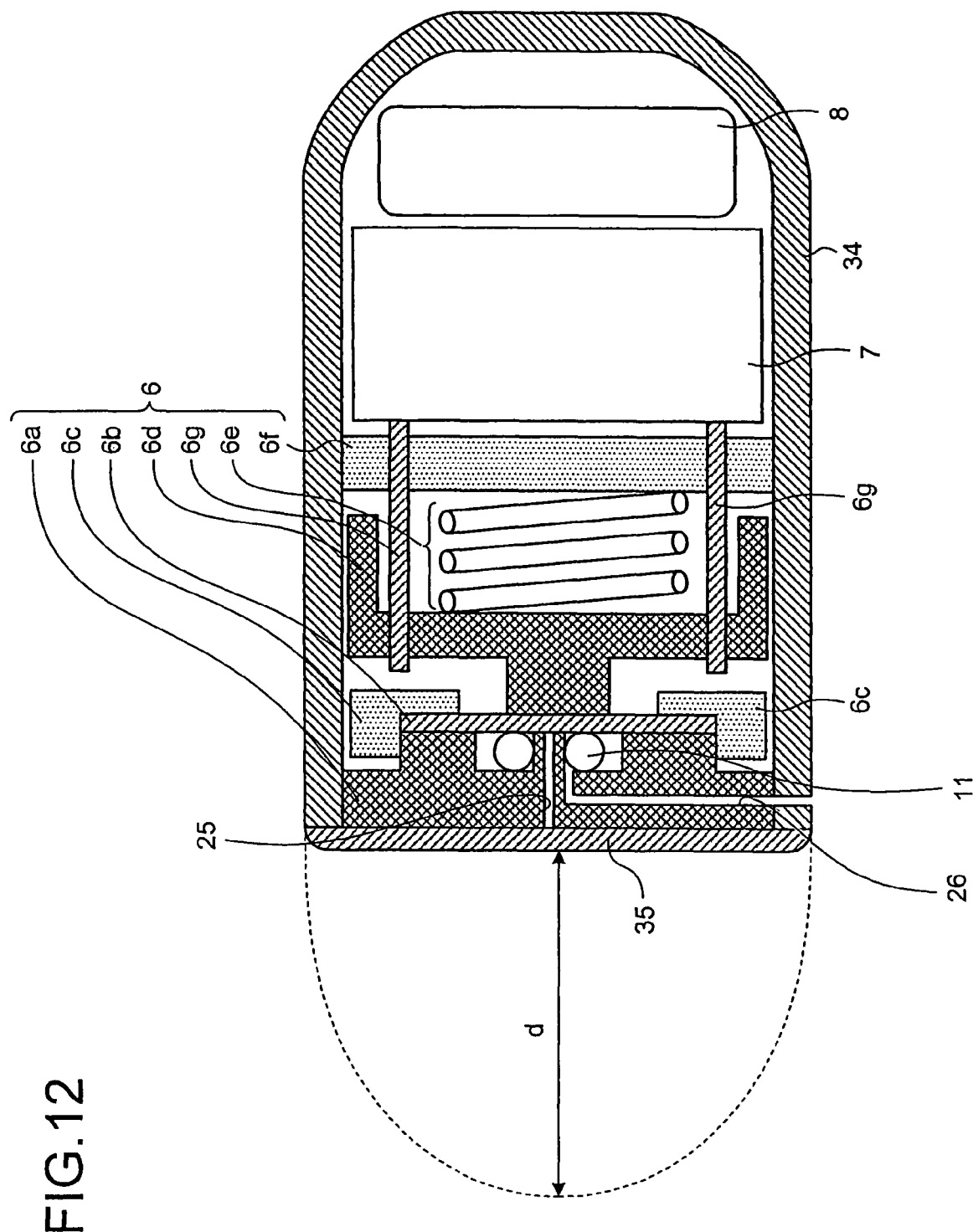
FIG. 12 is a schematic diagram showing the state of the body-insertable apparatus after discharging fluid.

FIG. 12 is a schematic diagram of the body-insertable apparatus according to the fourth embodiment showing the state after discharging fluid such as medication stored in the storage chamber 36. According to the fourth embodiment, the stored fluid is discharged by the contracting operation of the balloon member 35 as the fluid generating unit. The volume of the storage chamber 36 after completing the discharging is almost 0. As shown in FIG. 12, the expansion and contraction film constructing the balloon member 35 is contacted with the back surface of the sheet holding substrate 6a.

According to the fourth embodiment, the longitudinal length of the body-insertable apparatus is reduced by a predetermined length d before and after discharging fluid and the volume is reduced according to the reduction of the length. As is well known, the body-insertable apparatus is made smaller to reduce the load for the body. The body-insertable apparatus according to the fourth embodiment can reduce the load for the body by decreasing the occupied volume in the body after the fluid discharging.

The present invention of the first to fourth embodiments and the modification is described above. It is not appropriate to understand the present invention by being limited to the above embodiments. Those skilled in the art can consider various embodiments and modifications. For instance, according to the first embodiment, the body-insertable apparatus has the communication adjusting mechanism 6 using the spring member 6e and the shape memory member 6g. Other configuration can use any communication adjusting mechanism which can adjust the communication state between the inside of the balloon member 3 and the outer space based on control of the control circuit 7. The first embodiment also employs the configuration in which the control circuit 7 is used as a control unit and the communication adjusting mechanism 6 adjusts the communication state based on an electric current output from the control circuit 7. The control circuit 7 may be integrated with the communication adjusting mechanism 6 to use a control unit directly controlling the communication state.

According to the first embodiment, the balloon member 3 forming at least part of the outer wall portion of a predetermined closed space is used as the flow generating unit. The present invention needs not be limited to such configuration. The flow generating unit of the present invention which has the expansion and contraction film in at least part thereof and can generate a flow state of fluid by the expanding and contracting operation of the expansion and contraction film may not be formed in a balloon shape. Specifically, according to the first embodiment, the example in which a flow state is generated by the contracting operation of the expansion and contraction film is described. For instance, a flow state may be generated by the expanding operation in place of the contracting operation. In such case, the shape of the expansion and contraction film is changed to directly generate a flow state of fluid.

The body-insertable apparatus according to the present invention has the flow generating unit directly generating a flow state by the shape change of the expansion and contraction film with contraction. Unlike the conventional apparatus, the configuration such as the spring member for generating a flow state is unnecessary so that the configuration can be simplified.

A method for manufacturing the body-insertable apparatus according to the present invention, with respect to the method for manufacturing the body-insertable apparatus which has the balloon member, the expansion and contraction film is arranged on the predetermined communication pipe forming part to contact and fix the outer circumferential portion of the arranged expansion and contraction film with the communication pipe forming part for forming the balloon member. The balloon member as the flow generating unit can be easily formed.

INDUSTRIAL APPLICABILITY

As described above, the body-insertable apparatus and the manufacturing method thereof according to the present invention are useful for making the body-insertable apparatus smaller. In particular, to take in fluid such as body fluid of the body or to discharge fluid such as medication in the body, the present invention is suitable for the body-insertable apparatus.

The invention claimed is:

1. A body-insertable apparatus that is introduced into a body and performs predetermined fluid in the body, comprising:
 a storage chamber formed inside an outer circumferential member of the body-insertable apparatus and storing the predetermined fluid;
 a flow generating unit that has an expansion and contraction film which contracts with changes in the shape of the expansion and contraction film, and generates a flow state of the predetermined fluid based on a negative pressure emerged between the storage chamber and the body based on the contracting of the expansion and contraction film; and
 a control unit that controls the contracting operation of the expansion and contraction film;

a first communication pipe communicating with the storage chamber or the inside of the expansion and contraction film, one end of the first communication pipe being opened to the storage chamber or the inside of the expansion and contraction film; and a second communication pipe communicating the first communication pipe with the outside of the body-insertable apparatus, one end of the second communication pipe being opened to the outside of the body-insertable apparatus, an other end of the second communication pipe being opened to an other end of the first communication pipe;

wherein the flow generating unit has a communication adjusting mechanism for adjusting a communication state between the first communication pipe and the second communication pipe according to control of the control unit, and the communication adjusting mechanism includes:

a sheet holding substrate through which the first communication pipe and the second communication pipe pass, and including a concave region to which the other end of the first communication pipe and the other end of the second communication pipe are opened;

a sheet member that covers the concave region and directly controls the communication state between the other end of the first communication pipe and the other end of the second communication pipe, the other end of the first communication pipe and the other end of the second communication pipe being provided at one side of the sheet member; and a pressing member that is provided at an other side of the sheet member, and applies a predetermined pressing force against the sheet member so as to block the communication state between the other end of the first communication pipe and the other end of the second communication pipe according to the control of the control unit.

2. The body-insertable apparatus according to claim 1, wherein the expansion and contraction film is formed of elastic material.

3. The body-insertable apparatus according to claim 1, wherein the flow generating unit includes a balloon member that has a film-like member including in at least part thereof the expansion and contraction film, and that generates the flow state based on changes in an internal volume with the contracting.

4. The body-insertable apparatus according to claim 3, wherein an opening communicating a space region covered by an outer surface of the balloon member and an inner surface of the outer circumferential member formed to cover an outer surface of the balloon member with an outer space of the body-insertable apparatus is provided in part of the outer circumferential member.

5. The body-insertable apparatus according to claim 3, wherein the storage chamber has an outer wall formed by the balloon member and the outer circumferential member formed to be spaced at a predetermined distance from an outer surface of the balloon member in an outside of the balloon member so as to store the predetermined fluid in a space region covered by the outer surface of the balloon member and an inner surface of the outer circumferential member.

6. The body-insertable apparatus according to claim 5, wherein an opening communicating the storage chamber with an outer space of the body-insertable apparatus is provided in part of the outer circumferential member.

7. The body-insertable apparatus according to claim 1, wherein the communication adjusting mechanism includes:
    a spring member that generates the predetermined pressing force; and
    a shape memory member that changes the pressing force so as to communicate the other end of the first communication pipe and the other end of the second communication pipe according to the control of the control unit.

* * * * *